(12) United States Patent
Borevitz et al.

(10) Patent No.: US 6,573,432 B1
(45) Date of Patent: Jun. 3, 2003

(54) REGULATION OF ANTHOCYANIN PIGMENT PRODUCTION

(75) Inventors: Justin Borevitz, La Jolla, CA (US); Yiji Xia, San Diego, CA (US); Richard A. Dixon, Ardmore, OK (US); Christopher J. Lamb, Norfolk (GB)

(73) Assignees: The Samuel Roberts Noble Foundation, Inc., Ardmore, OK (US); The Salk Institute For Biological Studies, La Jolla, CA (US)

( * ) Notice: Subject to any disclaimer, the term of this patent is extended or adjusted under 35 U.S.C. 154(b) by 0 days.

(21) Appl. No.: 09/610,185

(22) Filed: Jul. 5, 2000

(51) Int. Cl.[7] .................... A01K 67/00; C07H 21/02; C07H 21/04

(52) U.S. Cl. .................. 800/295; 536/23.1; 536/23.2; 536/23.6; 536/24.1; 536/24.3; 536/24.33; 435/6; 435/69.1; 435/70.1; 435/410; 435/419; 530/370; 800/278

(58) Field of Search ................... 435/6, 69.1, 70.1, 435/410, 419, 320.1; 530/370; 536/23.1, 23.2, 23.6, 24.1, 24.3, 24.33; 800/278, 295

(56) References Cited

U.S. PATENT DOCUMENTS 5,972,643 A 10/1999 Lobanenkov et al. ...... 435/69.1

FOREIGN PATENT DOCUMENTS

| WO | WO 96/37609 | 11/1996 | ........... C12N/15/12 |
|---|---|---|---|
| WO | WO 98/13486 | 4/1998 | |
| WO | WO 01/32002 | 5/2001 | |

OTHER PUBLICATIONS

GenBank Accession No. AF062908 (Dec. 9, 1998).*
GenBank Accession No. AF062915 (Dec. 9, 1998).*
Houwelingen (The Plant Journal (1998) 13(1) 39–50).*
Abe et al., "Role of Arabidopsis MYC and MYB homologs in drought–and Abscisic acid—regulated gene expression," *The Plant Cell*, 9:1859–1868, 1997.
Borevitz et al., "Activation tagging identifies a conserved MYB regulator of Phenylpropanoid biosynthesis," *The Plant Cell*, 12:2383–2393, 2000.
EMBL Database Accession No. AF062915. Dec. 2, 1998.
Kirik et al., "Ectopic expression of a novel MYB gene modifies the architecture of Arabidopsis inflorescence," *The Plant Journal*, 13(6):729–742, 1998.
Bate, N.J., et al., *Plant Journal*, 16:561–569, (1998) "$C_6$–volatiles derived from the lipoxygenase pathway induce a subset of defense–related genes".
Blount, J.W., et al., *Plant Physiology*, 122:107–116, (2000) "Altering Expression of Cinnamic Acid 4–Hydroxylase in Transgenic Plants Provides Evidence for a Feedback Loop at the Entry Point into the Phenylpropanoid Pathway".

Deikman, J., et al., *Plant Physiology*, 108:47–57, (1995) "Induction of Anthocyanin Accumulation by Cytokinins in *Arabidopsis thaliana*".
Dixon, R.A., et al., *Plant Cell*, 7:1085–1097, (1995) "Stress– Induced Phenylpropanoid Metabolism".
Ehlting, J., et al., *Plant Journal*, 19:9–20, (1999) "Three 4–coumararate:coenzyme A ligases in *Arabidopsis thaliana* represent two evolutionarily divergent classes in angiosperms".
Glabgen, W.E., et al., *Planta*, 204:490–498, (1998) "Regulation of enzymes involved in anthocyanin biosynthesis in carrot cell cultures in response to treatment with ultraviolet light and fungal elicitors".
Graham, T.L., et al., *Plant Physiol. Biochem.*, 36:135–144, (1998) "Flavonoid and flavonol glycoside metabolism in Arabidopsis".
Inoue, K., et al., *Plant Physiology*, 117:761–770, (1998) "Developmental Expression and Substrate Specificities of Alfalfa Caffeic Acid 3–O–Methyltransferase and Caffeoyl Coenzyme A 3–O–Methyltransferase in Relation to Lignification".
Jin, H., et al., *Plant Molecular Biology*, 41:577–595, (1999) "Multifunctionality and diversity within the plant MYB–gene family".
Kranz, H.D., et al., *Plant Journal*, 16:263–276, (1998) "Towards functional characterisation of the members of the R2R3–MYB gene family from *Arabidopsis thaliana*".
Leyva, A., et al., *Plant Physiology*, 108:39–46, (1995) "Low Temperature Induces the Accumulation of *Phenylalanine Ammonia–Lyase* and *Chalcone Synthase* mRNAs of *Arabidopsis thaliana* in a Light–Dependent Manner".
Lo, S.C., et al., *Plant Physiology*, 116:979–989, (1998) "Reduction of Light–Induced Anthocyanin Accumulation in Inoculated *Sorghum Mesocotyls*".
Loidl, A., et al., *Critical Reviews in Oncogenesis*, 7:49–64, (1996) "Oncogene– and Tumor–Suppressor Gene–Related Proteins in Plants and Fungi".
Lu, F., et al., *Agric. Food Chem.*, 45:2590–2592, (1997) "Derivation Followed by Reductive Cleavage (DFRC Method), a New Method for Lignin Analysis: Protocol for Analysis of DFRC Monomers".
Noh, B., et al., *Plant Physiology*, 116:503–509, (1998) "Anion Channels and the Stimulation of Anthocyanin Accumulation by Blue Light in Arabidopsis Seedlings".

(List continued on next page.)

Primary Examiner—Kenneth R. Horlick
Assistant Examiner—Alexander H. Spiegler
(74) Attorney, Agent, or Firm—Fulbright & Jaworski L.L.P.

(57) ABSTRACT

A method for determining gene expression in transgenic plants is disclosed. This method includes providing expression vectors having the PAP1 or PAP2 gene linked to an expressed gene of interest. If the expression vector is activated, the PAP1 or PAP2 genes confer a purple pigmentation to the transgenic plant. Thus, plants that have been successfully transformed are easily identifiable by visual inspection.

14 Claims, 2 Drawing Sheets

OTHER PUBLICATIONS

Romero, I., et al., *Plant Journal*, 14:273–284, (1998) "More than 80 R2R3–MYB regulatory genes in the genome of *Arabidopsis thaliana*".

Solecka, D., et al., *Plant Physiol. Biochem.*, 37:491–496, (1999) "Phenylpropanoid and anthocyanin changes in low–temperature treated winter oilseed rape laves".

Schuch, W., et al., Soc. for Exp. Biol. Seminar Series 49: *Inducible Plant Proteins* (J.L. Wray, ed.) Cambridge Univ. Press, pp. 97–111, (1992) "Expression and manipulation of genes involved in phenylpropanoid biosynthesis".

Weigel, Detlef, et al., *Plant Physiology*, 122:1003–1013, (2000) "Activation Tagging in Arabidopsis".

* cited by examiner

REGULATION OF ANTHOCYANIN PIGMENT PRODUCTION

FIELD OF THE INVENTION

The present invention generally relates to MYB-like transcription factors that regulate the production of anthocyanin pigment. More specifically, the invention relates to PAP1 and PAP2 genes that can be used to increase pigmentation specifically in the petals, to identify plants under stress, and to upregulate the phenylpropanoid pathway.

BACKGROUND OF THE INVENTION

Plants produce an enormous array of natural products. Ethnobotany and limited screens of medicinal plants indicate that among this huge repertoire of chemical diversity are many potentially useful bioactive structural principles for developing novel drugs, flavors, fragrances and other specialty chemicals. Unfortunately, these complex natural products usually occur at very low abundance and with a restricted tissue distribution. Moreover, almost all of this phytochemical biodiversity resides in exotic, uncultivated species. While important plant-based drugs such as Taxol®, vinblastine, and vincristine have been discovered, the development of rational approaches for the generation of useful amounts of complex natural products for industrial evaluation remains an unsolved problem.

In particular, an intense 30-year effort on cell and tissue culture of medicinal plants has failed to generate useful levels of complex products either for the commercial production of established drugs in vitro, or for high throughput, multiplex screening of phytochemical biodiversity. This likely reflects the stringent spatial and temporal transcriptional controls governing the biosynthesis of specific natural products during plant development. Transgenic manipulation to override these genetic controls may thus provide the key to enhancing natural product biosynthesis for industrial evaluation and exploitation.

Activation tagging with the enhancer from the cauliflower mosaic virus (CaMV) 35S transcript promoter (35Se) is an emerging technology in plant functional genomics (Weigel, et al., *Plant Physiol.*, 122:1003, 2000). This approach uses *Agrobacterium tumefaciens*-mediated transformation to create transgenic plants in which the transferred-DNA (T-DNA) containing the 35Se at its right border is spliced into the plant genome at random sites. In each independent transgenic line, the 35Se strongly activates the plant gene to which, by chance, it lies adjacent. Activation of a gene in this fashion often leads to observable effects on the modified plant, providing important clues about the function of the activated gene. Screening large collections of independent activation tagged lines thus represents a powerful way of surveying the genome and isolating genes affecting traits of interest.

A universal and well-studied flavonoid natural product is the floral pigment anthocyanin. The anthocyanin biosynthetic pathway is well characterized and many key regulators of the pathway have also been discovered. Genetic screens in Arabidopsis for loss of anthocyanin pigments were performed by screening for loss of pigmentation in the seed coat (testa). Many transparent testa loci correspond to anthocyanin biosynthetic genes. Transparent Testa Glaborous1 is a regulatory gene that encodes a WD40 repeat protein and whose mutant phenotype has pleiotropic defects including loss of anthocyanins and trichomes, and increased root hairs.

The WD40 repeat protein An11 in petunia also controls anthocyanin production. Anthocyanin production in many species is controlled by MYB and bHLH transcription factors. The maize MYB proteins C1 and pl interact with the bHLH proteins of the R/B family to regulate transcription of biosynthetic genes beginning with chalcone synthase (CHS). In petunia, the bHLH locus, An1 and Jaf13, and the MYB An2 locus, direct pigmentation. In Arabidopsis many bHLH and MYB genes exist but few have known functions. The MYB genes GL1 and CPC are involved in trichome and root hair initiation respectively. An Arabidopsis MYB gene involved in anthocyanin production heretofore had not been identified.

SUMMARY OF THE INVENTION

Embodiments of the invention provide an isolated PAP1 or PAP2 gene, or an active segment thereof. In some aspects, the invention provides a nucleic acid construct including a PAP1 or PAP2 gene, or an active segment thereof. In the construct the PAP1 or PAP2 gene can be operably linked to a promoter. The PAP1 gene can include the nucleotide sequence of SEQ ID NO:1; the PAP2 gene can include the nucleotide sequence of SEQ ID NO:3. The construct can encode a fusion protein including a PAP1 or PAP2 polypeptide, or an active segment thereof. The invention further provides a cell including the construct of this aspect of the invention. In another aspect, the invention provides a purified PAP1 or PAP2 polypeptide, or an active segment thereof. The polypeptide can include the amino acid sequence of SEQ ID NO:2 or SEQ ID NO:4 and the polypeptide can be encoded by a nucleotide sequence including SEQ ID NO:1 or SEQ ID NO:3.

Another aspect of the invention is a transgenic plant including a nucleic acid construct having a PAP1 or PAP2 gene, or an active segment thereof. The gene can include the nucleotide sequence of SEQ ID NO:1 or SEQ ID NO:3; the plant can be *Arabidopsis thaliana*. The expression of the PAP1 or PAP2 gene can be tissue specific. In the transgenic plant, the tissue can be selected from the group consisting of, floral tissue, leaf, stem, root, cortex, meristem and cambium. PAP1, PAP2, or a segment thereof, can be overexpressed in floral organs, producing modified floral pigmentation, which can involve control of pigment production by action of a transposon.

In yet another aspect of the invention, there is provided a method of screening for gene expression including: providing a nucleic acid construct including a PAP1 or PAP2 gene or an active segment thereof, functionally fused to a gene of interest; transforming a plant cell with the nucleic acid construct to produce a transgenic plant or transgenic cell culture; and determining whether the gene of interest can be expressed based on the color of the transgenic plant or transgenic cell culture. The expression can be tissue-specific; the construct can include the nucleotide sequence of SEQ ID NO:1 or SEQ ID NO:3; the plant can be any plant amenable to transformation such as, for example, *Arabidopsis thaliana*. Another embodiment of this aspect of the invention is a method of identifying a gene in a biosynthetic pathway in a plant, including the steps of: transforming a population of plants or plant cells with a nucleic acid construct including an activation tag; screening the population to detect an individual having an increased accumulation of a product or an intermediate in the pathway; and identifying a gene of the biosynthetic pathway in the individual, based on proximity to the activation tag. The screening step can include chromatography to identify up-regulation of the product or intermediate in the pathway.

A preferred mode of chromatography is HPLC. The product of the biosynthetic pathway can be a pigment, and the screening step can include screening the population to detect an individual having an increased production of a pigment, a pigment-related protein, or a pigment-related product, and the gene identified can be a pigment gene or a pigment-related gene. The pigment-related protein can be selected from the group consisting of: PAL1, PAL2, PAL3, CAD, 4CL, CHS, CHI, DFR, and flavone-3-hydrolase. The pigment-related product can be selected from the group consisting of: coumaric acid, coumarate conjugate, synapic acid, ferulic acid, salicylic acid, and lignin.

Aspects of the invention further provide a method of characterizing an intermediate in a biosynthetic pathway including: identifying a gene by an embodiment of the methods previously mentioned; transforming a plant or plant cell with the gene or a derivative thereof; and characterizing the intermediate by screening the transgenic plant or plant cell for up-regulated or down-regulated products. Also provided is a method of detecting a stress condition in a plant, including: providing a population of plants overexpressing a PAP1 or PAP2 gene or an active segment thereof; monitoring one or more plants of the population for color change associated with anthocyanin pigmentation; and detecting a stress condition in a plant, based on the color change. The stress condition can be associated with a stress selected from the group consisting of: light stress, water stress, pH stress, salt stress, temperature stress, heavy metal stress, pathogen attack or infection, wounding, nutrient deficiency, herbivory, and abnormal hormone levels.

Still other aspects of the invention provide a method of detecting promoter activity within a plant cell, including: providing a nucleic acid construct including a PAP1 or PAP2 gene, or an active segment thereof, operably linked to and promotable by a nucleic acid sequence including a promoter region or an active segment thereof; causing the construct to be expressed in the plant cell; and detecting a color or color change associated with anthocyanin pigmentation, wherein the color or color change arises from activity of the promoter region or active segment thereof within the plant cell. The plant cell can correspond to a tissue of a whole plant, and expression of the promoter can be specific to the tissue. Likewise, the plant cell can correspond to a developmental stage or structure of a whole plant, and expression of the promoter can be specific to the developmental stage or structure. Also provided is a method of screening for plant cell transformation, including the steps of: providing a nucleic acid construct including the gene of interest linked to a PAP1 or PAP2 gene; transforming a plurality of plant cells with the expression vector; and determining which of the plurality of plant cells were successfully transformed, by reference to altered color of the plant cells. The transformed plant cells can be used to produce transgenic plants, and the altered color expression can be tissue-specific in the transgenic plants.

Further aspects of the invention include is a biological preparation for the up-regulation of anthocyanin production including one or more peptides selected from the group consisting of PAP1, PAP2, and a mixture thereof, in a biologically acceptable, non-toxic vehicle. Also provided is a method for the enhanced accumulation of a phenylpropanoid product in a plant including: constructing a transgenic plant overexpressing PAP1 or PAP2, or an active segment thereof, whereby production of a plurality of phenylpropanoid products and intermediates in the plant can be elevated. The method can further include the step of causing expression within the transgenic plant of a gene involved in a step in production of a selected phenylpropanoid product, whereby elevated production of the plurality of phenylpropanoid products and intermediates favors enhanced accumulation of the selected product. The transgenic plant can be of a taxon that is characteristic for production of a selected phenylpropanoid product, and accumulation of the selected product can be enhanced by elevated production of the plurality of phenylpropanoid products and intermediates in the plant. For example, the plant can be *Lycopersicon esculentum*, and the selected product can be a lycopene; the plant can be *Sesamum indicum*, and the selected product can be sesamin and/or sesamolin; the plant can be any nitrogen fixing species, and wherein the selected product can be acetosyringone. In yet another aspect, the invention provides a system for expression of a gene of interest, the system including a PAP1 or PAP2 gene, or an active segment thereof, and a promoter including an anthocyanin myb binding site, wherein the promoter is operably linked to the gene of interest, wherein the product of the PAP1 or PAP2 gene or segment thereof binds to the myb binding site and causes expression of the gene of interest.

DETAILED DESCRIPTION

Embodiments of the present invention provide regulatory genes and gene products associated with production of anthocyanin pigmentation in plants. Anthocyanin is a product of the phenylpropanoid pathway, as are many other natural products, some of which are associated with plant stress. Many products of the phenylpropanoid pathway have great potential in pharmaceutical applications. Genes with a key role in regulation of various steps in the phenylpropanoid pathway thus provide a useful tool for enhancing accumulation of important natural products, detection of plant stress, manipulation of coloration patterns and/or intensities in ornamental plants, analysis of promoter strength and specificity, and other uses discussed further herein. In addition, embodiments of the invention provide methods and materials for manipulation of plants to enhance expression levels in other biosynthetic pathways that normally are tightly regulated.

Activation tagging was used to isolate a bright purple mutation, pap1-D (production of anthocyanin pigment), in which genes encoding enzymes involved in the biosynthesis of phenylpropanoid natural products exhibit massive and widespread activation throughout plant development. The pap1-D phenotype, which is caused by overexpression of a gene encoding a MYB transcription factor, indicates that activation tagging can be used to overcome the stringent genetic controls regulating the developmental accumulation of specific natural products. These findings disclose a new approach to phytochemical bioprospecting through the generation of massively enriched tissue sources for drug screening and for the isolation of the underlying regulatory and biosynthetic genes.

Embodiments of the invention employ overexpressed PAP1 (SEQ ID NO:1) and PAP2 (SEQ ID NO:3) genes in a variety of methods and products. Some embodiments include the use of PAP1 and PAP2 to increase pigmentation in plants, with or without tissue specificity. In addition, some embodiments use PAP1 and/or PAP2 as reporter genes, for analysis of the expression pattern of a promoter of interest. Still other embodiments overexpress PAP1 and/or PAP2 to increase flux through the phenylpropanoid pathway, facilitating identification of other intermediates in that pathway or accumulation of important end products. The techniques used to identify PAP1 are also applicable to identification of other proteins involved in pigment production or regulation of other important biosynthetic pathways. Likewise, global regulators of phenylpropanoid biosynthesis can be transferred to other plant species in which bioactive natural products can be made in large amounts. Other embodiments and uses of the invention will become apparent to those of skill in the art from the examples and results disclosed herein.

Embodiments of the invention provide polynucleotides that include the PAP1 or PAP2 genes, or active segments or mutants of these genes that can regulate anthocyanin production. These polynucleotides can be in the form of a linear molecule of DNA or RNA or they can be part of a larger construct, such as one that can function as a vector. It is known to those of skill in the art that a vector can be, for example, a plasmid, a virus, a bacteriophage, or any of several modifications thereof. The vector can be an expression vector or it can be a vector that simply carries the polynucleotide. Expression can be controlled by the PAP1 or PAP2 promoter, or by a variety of other promoters, depending on the intended use of the construct.

Other tissue-specific plant or plant viral promoters can be of significant interest, particularly in the production of a phenotypically unusual plant. Such promoters can be useful, for example, when color expression in only one plant structure, or variegated expression, is desired. Moreover, such an expression system can be used to regulate the production of proteins during development of the plant. For example, a color change can be designed to occur only during later maturation stages of the plant life cycle.

A further embodiment of the invention is a PAP1 or PAP2 polypeptide (SEQ ID NO:2 or SEQ ID NO:4, respectively), or active segments or mutants of these polypeptides. Of particular interest is the use of the polypeptides to treat a particular plant tissue. For example, the PAP1 or PAP2 polypeptides can be introduced to a plant to cause transient color changes, or transient activation of certain intermediates in the pigmentation pathway.

For applications in which PAP1 or PAP2 protein is used to effect a transient activity in a plant, preferably the PAP1 or PAP2 exists in a purified state. Purification of PAP1 and PAP2 is accomplished by any of several techniques, such as, for example, affinity purification, chromatography, and immunoprecipitation. For immunoprecipitation, Western blotting, and other procedures or assays that require use of an antiserum capable of recognizing PAP1 or PAP2, preparation of a polyclonal serum is accomplished by standard techniques using partially purified proteins or synthetic fragments based on the amino acid sequences of the proteins.

Other embodiments of the invention provide methods and materials for identifying stress in plants that overexpress the PAP1 or PAP2 gene. (Unless indicated otherwise, mention of PAP1 or PAP2 genes in connection with embodiments of the invention also refers to one or more active segments of either gene.) Such genes can function as phenotypic reporters of stress conditions. This is due to the fact that many stress conditions are associated with elevated expression of anthocyanin, and the increased availability of anthocyanin precursors in plants that overexpress PAP1 or PAP2 makes the stress-induced accumulation of anthocyanin more evident under even mild stress conditions. When the plant begins to experience a variety of stresses, including increased light, drought, UV light, pH change, change in salt conditions, increased heavy metal concentrations, wounding, nutrient deficiency, herbivorous insect attack, low temperature, abnormally high cytokinin production, plant pathogen infection and the like, the plant activates PAP1 and/or PAP2 and exhibits purple or red coloration depending on the type of plant and the nature of the stress. Plants overexpressing PAP1 or PAP2 can be useful in timecourse studies or studies of other factors in controlled experiments relating to any single stress, or to the synergistic or antagonistic interactions of multiple plant stresses.

Under mild stress, a plant overexpressing PAP1 or PAP2 can exhibit a detectable change in color. This provides a visual indication of plant stress that is easily recognizable, and that also can in some cases be quantifiable. Accordingly, by this method, plants can be tested for stress due to, for example, any of the stresses mentioned above.

PAP1 or PAP2 overexpression can also be useful in developing or enhancing desirable coloration in ornamental plants for commercial sales. As an example, in one embodiment of this aspect of the invention, plants can be grown under mild stress conditions to produce foliage, flowers, or other structures having desired colors or unusual intensities or shades of color. Such mild stresses as moderate water stress or salt stress are easily achieved in large scale commercial settings, and can be effective in many cases to manipulate anthocyanin pigmentation in ornamental plants.

In further embodiments, PAP1 or PAP2 overexpression can be activated or eliminated based on the insertion or excision of transposable elements. Transposable element activity of this nature can produce flowers or other plant parts having a variegated appearance or displaying other patterns, depending on the nature of the transposon activity. In such embodiments, a preferred transposon for use in ornamental plants is the Ac transposon from maize.

Another embodiment of the invention is a method for sensitizing plants to stress. In this embodiment, plants are transformed with the PAP1 or PAP2 gene so that they become more responsive to stress-induced phenotypic changes. As discussed above, the PAP1 and PAP2 genes are related to the protooncogene MYB, which is involved in plant metabolic pathways, such as induction of stress related genes. Because of this relationship, and the fact that anthocyanin is associated with responses to stress in plants, introduction of PAP1 or PAP2 can sensitize plants to respond more quickly to a stress condition in ways that are physiologically significant, as well as in ways of ornamental significance as discussed above.

Accordingly, important crops, such as fruits, vegetables, and tobacco can be made more hearty by transformation with PAP1 or PAP2. For example, tobacco plants can be transformed with PAP1 or PAP2 by the methods described in the following examples. In comparisons of transformed and non-transformed plants, those overexpressing PAP1 or PAP2 are more resistant to various stresses than the non-transformed plants.

Another embodiment of the invention is a transgenic plant that is inducible to activate PAP1 or PAP2 under control of an inducible promoter. Such plants can be induced, for example, by small molecules such as steroid hormones, to express the PAP1 or PAP2 protein. Because expression of the PAP1 or PAP2 proteins can lead to sensitization of shock conditions, this mechanism can provide an inducible system for sensitizing plants to an upcoming shock. One method for inducing synthesis of PAP1 or PAP2 is to link the hormone response element that is the target of the HeCR gene product to the PAP1 or PAP2 gene. As disclosed in PCT publication WO 96/37609, a hormone-controlled gene switch is created by linking the HeCR targeted hormone response element (HRE) to a heterologous gene. Activation by a steroidal or non-steroidal hormone in the transformed plant can then induce transcription of PAP1 or PAP2.

Because PAP1 and PAP2 control the expression of an easily identified pigment, they can be used as plant reporter genes in a manner similar to well-known reporters such as CAT or Green Fluorescent Protein (Aurora). Therefore, PAP1 or PAP2 can be functionally fused to a promoter of interest and expressed in a plant. When the promoter is active, the transformed plant exhibits a change in color as an indicator of promoter activity. This system can provide information on the tissue-specific expression of the promoter being studied, or it can provide information on other expression patterns that are manifest using the system, such as temporal expression, inducible expression, developmentally-regulated expression, and the like. Tissue-specific expression can thus be monitored visually by the color of the plant tissue. Moreover, in many cases promoter strength can be determined quantitatively or semi-quantitatively via colorimetric assays of plant structures, tissues, cells, or extracts.

The anthocyanin phenylpropanoid pathway, like many molecular pathways, still remains to be completely characterized in model systems, and is variable among plant species. In many plants, intermediates as well as end products in the pathway or branches thereof are still to be identified. Therefore, because PAP1 and PAP2 activate this pathway, these genes can be used to identify intermediates and products that are expressed at low levels, as well as those that are expressed transiently. The pathway can also be activated by PAP1 or PAP2 in tissue culture or in a whole plant, and intermediates or products can be identified in a variety of ways. One preferred technique involves the use of HPLC as presented in the examples below.

Some known targets of PAP1 and PAP2 include phenylalanine ammonia lyase (PAL 1, 2, or 3), chalcone synthase (CHS), dihydroflavonol reductase (DFR), flavonone-3-hydroxylase, chalcone isomerase, cinnamyl alcohol dehydrogenase (CAD), 4-coumarate:CoAligase (4CL), and chalcone isomerase (CHI). Therefore, in addition to identifying further targets as outlined above, a plant that overexpresses a useful product can be used for isolation of that product, for further investigation of the product in the biology of the plant or as a candidate for screening of pharmacological activity of natural products. Accordingly, a plant having increased phenylpropanoid production caused by overexpression of PAP1 or PAP2, and a plant expressing various products of the phenylpropanoid pathway, are embodiments of the invention.

In preferred embodiments of this aspect of the invention, cells or calli having an altered color phenotype are cultured under suitable conditions to produce a complete transgenic plant. Such a plant is useful for further study of the gene of interest. Moreover, transgenic plants that produce phenylpropanoids of commercial interest can be mass-cultivated so as to achieve an economically feasible means for the production of these molecules.

The method used for identifying PAP1 and PAP2 in plants can be generally applicable for any pigment or other phenotypically identifiable pathways. Therefore, in some embodiments of the inventions, activation tagging (as previously described in Weigel, et al., *Plant Physiol.*, 122:1003, 2000) is performed on a plant, clones with an altered pigment or other visible phenotype are selected, and the tagged gene associated with the altered phenotype is identified. Alternatively, HPLC can be used to identify a change in expression of a known pathway intermediate or product.

When a new gene playing a role in a biosynthetic pathway is identified by activation tagging, its function can be further characterized, according to conventional methods, by creating a transgenic plant overexpressing that gene. Upon overexpression of the gene in the transgenic plant, HPLC of natural products or other natural product assays can indicate accumulation of one or more intermediates or end products, which aid in elucidating the function of the gene.

A further embodiment of the invention is a method for expressing a protein of interest in a plant. This involves constructing a transgenic plant that expresses the protein under control of the PAP1 or PAP2 promoter. Alternatively, the protein of interest can be constructed to be a fusion protein of PAP1 or PAP2 or an active segment thereof. Fusion proteins that include PAP1, PAP2, or an active segment thereof, can be made in a variety of ways. In some embodiments, a chimeric protein is constructed wherein the C-terminal domain of the protein is a complete or nearly complete PAP1 or PAP2 with the N-terminus being a suitable protein of interest. Likewise, in other embodiments, the N-terminus is the PAP1 or PAP2 protein or fragment thereof, and the C-terminus is the protein of interest. Once the appropriate construct is made, the protein of interest is then be overexpressed in a convenient tissue of the plant, which is harvested and extracted to isolate the protein of interest.

In a further embodiment, the invention provides a system for expression of a gene of interest based on the activation by PAP1 or PAP2 genes of promoters having a myb or myb-like binding site. In these embodiments, a promoter having a myb binding site is operably linked to a gene of interest and expressed in a transgenic plant. Likewise, a PAP1 or PAP2 gene, or an active fragment thereof, can be under control of a tissue-specific promoter, a temporally regulated promoter, a developmentally regulated promoter, an inducible promoter, or other promoters known in the art. With this dual regulation system, it is possible to finely attenuate the localization and timing of expression of the gene of interest.

Certain embodiments of the invention relate to products and methods for detecting gene insertion in transgenic plants. In such embodiments, gene insertion is detected by visualization of a color change in a plant having PAP1 or PAP2 co-transformed with a gene of interest. For example, a Ti plasmid carrying a gene of interest closely associated with PAP1 or PAP2 can be used in a plant transformation protocol. The presence of an altered color phenotype in certain cells or calli is a reliable indication that the gene of interest is also present.

Accumulation of phenylpropanoid products during development is under tight transcriptional regulation and the pap1-D phenotype represents a striking override of these stringent genetic controls. Specific branches of the overall pathway are controlled by separate sets of transcription factors. For example, the maize myb genes C1 and pl are involved in the regulation of anthocyanin synthesis from chs onward, but do not regulate pal and other genes of the upstream central pathway, whereas P independently controls the 3-deoxy flavonoid branch pathway. In contrast, the pap1-D phenotype, which results from overexpression of the PAP1 MYB transcription factor, reflects massively enhanced expression of pal as well as chs, dfr and gst. This broad transcriptional activation of the overall pathway is accompanied by a correspondingly broad pattern of enhanced product accumulation with elevated levels of lignin, wall bound hydroxycinnamic acid esters, flavonols and anthocyanins. Moreover, pathway activation in pap1-D was observed in all vegetative organs and maintained throughout development, in marked contrast to the activation of individual branch pathways at defined developmental stages and with characteristic cell-type, tissue-type and organ specificities in wild type plants.

MYB genes contribute to the control of flavonoid biosynthesis in a wide range of plant species, often in combination with other regulatory genes. In maize c1 and pl but not P require R and B, encoding basic helix-loop-helix proteins, to activate transcription of maize flavonoid biosynthetic genes. Basic helix-loop-helix proteins and MYB proteins also function together in the control of flower pigmentation in snapdragon and petunia. Moreover, WD40 proteins are important for MYB control of flavonoid biosynthesis in both Arabidopsis and petunia and the pap1-D phenotypes require the WD40 gene TTG1. Despite the stringent and often complex genetic control of phenylpropanoid biosynthesis, strong ectopic expression of PAP1 in the pap1-D line was sufficient to hyperactivate the pathway, reminiscent of the enhancement of flavonoid biosynthesis by deliberate ectopic expression of P in suspension cultured maize cells. The pap1-D phenotypes may reflect involvement of PAP1 as the limiting factor in a novel regulatory circuit with atypically broad control functions in phenylpropanoid biosynthesis or functional spillover from one regulatory circuit to related circuits when PAP1 is massively overexpressed.

Activation tagging thus can be used to generate novel gain-of-function mutations affecting complex biosynthetic pathways under polygenic control and hence disclose a powerful new approach for the isolation of genes regulating plant natural product biosynthesis. Loss-of-function screens for transparent testa have been saturated and no mutations map to the PAP1 or PAP2 loci. Moreover, examination of >100 PAP1 antisense lines showed no visible phenotype and the similar overexpression phenotypes of PAP1 and PAP2 suggest that these genes may be functionally redundant such that only an activation tagging or other gain-of-function screen could have readily revealed key attributes.

Activation tagging as a gene discovery tool based on gain-of-function is intrinsically oriented towards biotechnological utility and the ability to hyperactivate a biosynthetic pathway leading to the enhanced accumulation of several distinct sub-classes of natural products has several important potential applications. Thus hyperactivated tissues or organs provide massively enriched sources for passage through multiplex drug screens with the potential for discovery of novel activities based on combinatorial effects arising from complex mixtures as well as convenient isolation and characterization of individual bioactive components. This approach can be augmented by feeding studies using pathway intermediates or synthetic derivatives. Moreover, hyperactivation of phenylpropanoid biosynthesis in pap1-D reflects a massively enhanced expression of genes encoding pathway enzymes and hence these tissues provide a correspondingly enriched source for the isolation of cDNAs encoding key biosynthetic enzymes not readily identified by biochemical approaches.

While the plant kingdom contains a remarkable diversity of natural products, the underlying pathway regulatory mechanisms are at least partially conserved between species. For example the maize anthocyanin regulatory gene R functions appropriately when expressed in Arabidopsis or tobacco. Likewise ectopic expression of PAP1 or PAP2 in transgenic tobacco caused similar phenotypes to those observed in Arabidopsis. Hence convenient, readily transformed genetic model species such as Arabidopsis can be used to isolate candidate regulatory genes for direct evaluation in medicinal plants and other exotic species or as a platform for the identification of orthologs and potentially useful related genes in target species.

The discovery of pap1-D among a large collection of activation tagged lines was possible because hyperactivation of PAP1 enhanced the accumulation of anthocyanin pigments which were readily scorable. A number of other plant natural products e.g. the isoprenoids lycopene and carotene and the alkaloid sanguinarine are also colored. Thus it is now possible to make transgenic plants expressing readily screenable marker genes under the control of promoters from genes encoding enzymes involved in the biosynthesis of natural products of interest.

The following examples are intended for illustration purposes only, and should not be construed as limiting the scope of the invention in any way.

EXAMPLES

Example 1

Activation Tagging of *Arabidopsis thaliana*

Activation tagging, a gain of function screen, was used to identify PAP1 in Arabidopsis. Activation Tagging allows screening for dominant mutations in the $T_1$ generation where each plant is the result of at least one unique insertion event. An important advantage of this approach is that genes that are essential or act redundantly can be discovered.

An Agrobacterium-mediated plant transformation protocol was used to make pMN-PAP1 and 35S::PAP2 transgenic plants. A PAP1 genomic fragment was PCR-amplified and inserted into the activation tagging vector pMN20-2 (vector described in Weigel et al. *Plant Physiol.* 122:1003, 2000). 35S::PAP1 is the PCR-amplified PAP1 cDNA inserted into pCHF3 which is a pPZP211-based plant expression vector. Similarly 35S::PAP2 is the PAP2 cDNA cloned into pCHF3. Agrobacterium was grown for 2 days at 28° C. in YEP with appropriate antibiotics, pelleted and resuspended in 2 volumes water with 200 ul/L silwet 100 (Lehle Seeds, Round Rock, Tex.). An Agrobacterium suspension was applied to flowering Arabidopsis plants at weekly intervals with a spray bottle. Plants were kept humid in flats with lids for 1 day after spraying. A minimum of 2% transformation efficiency was consistently observed. Tobacco transformation was performed similarly, except that 0.02% Silwet-L77 was used.

Arabidopsis plants were grown in growth rooms at 22° C. in long days (16 hours light) or short days (9 h light) and received 250 $\mu$E of light from 3×35 W cool white bulbs and 1×35 W Sylvania Grow Lux bulb. Plants grown in low light conditions received 150 $\mu$E of light in the growth room under 1 neutral shade cloth. Tobacco plants were regenerated under 24 h light conditions at 25° C. and then transferred to the greenhouse.

Approximately 5,000 activation-tagged primary lines of *Arabidopsis thaliana* were generated using pSKI015, which contains 4 copies of 35Se and the Basta resistance gene. A single bright purple plant was observed and its seeds were collected for progeny analysis.

Example 2
Isolation and Characterization of a papI-D Mutant $T_2$ plants from the bright purple plant identified by the activation tagging of *A. thaliana* segregated the characteristic purple coloration in a 3:1 ratio consistent with this trait being determined by a single dominant allele. The mutant was named pap1-D for Production of Anthocyanin Pigment-Dominant. The purple coloration was most pronounced when plants were grown under high light intensities as compared to lower light intensities. Pigmentation was increased under other stressful conditions such as drought. The whole plant, including roots, primary and secondary branches, leaves, cauline leaves, as well as sepals, stamens, and carpels, had enhanced pigmentation compared to Col, the wild-type control. Except for very weak pigmentation in flower petals, enhanced pigmentation was observed throughout development. No other morphological phenotypes were observed.

Example 3
Expression of Phenylpropanoid Pathway Products in the papI-D Mutant

Since anthocyanins are a sub-class of flavonoid natural products derived from the phenylpropanoid skeleton, the expression of phenylpropanoid biosynthetic genes and the accumulation of pathway products were examined.

Southern and Northern Blot Analysis

DNA and RNA blot hybridizations were performed according to standard procedures. RNA samples were from vegetative leaves of pap1-D and Col-0 plants grown in short days for 4 weeks and long days for 2 weeks. Probes were full length cDNA fragments of PAP1, GST, UBI. The CHS probe was a PCR product amplified using the primers:

5'-TGGTCTCCGTCCTTCCGTCAA (SEQ ID NO:5), and

5'-CCCTCAAATGTCCGTCTATGGAA (SEQ ID NO:6).

The PAL probe was a PCR product amplified using the primers:

5'-CTATACGCTTACCTACCAACAA-AC (SEQ ID NO:7) and

5'-TCTCCGATGAGAAGTAGCACCAA (SEQ ID NO:8).

Northern blot analysis showed a massive enhancement of the expression of phenylpropanoid biosynthetic genes in pap1-D plants. The levels of transcripts encoding chalcone synthase and dihydroflavonol reductase, two key biosynthetic enzymes in the branch pathway specific for anthocyanins and other flavonoids, were dramatically higher in pap1-D plants than in Col plants. Transcripts encoding glutathione S-transferase, which has been implicated in the secretion of flavonoids into the vacuole, were at correspondingly elevated levels. Moreover, the accumulation of transcripts encoding phenylalanine ammonia-lyase, the first enzyme of the overall phenylpropanoid biosynthetic pathway, was also enhanced, suggesting that pathway activation was not confined to the flavonoid branch.

In order to determine how the increased expression of phenylpropanoid biosynthetic genes affected the levels and complexity of natural products, total anthocyanin levels, PAL enzyme activity, secondary metabolites, and lignin concentration were examined as follows:

Enzyme Assays

PAL activity was measured by a microcuvette spectrophotometric assay (Blount, J. W. et al. *Plant Physiol.* 122, 107–116 (2000)). COMT and CCOMT activities were assayed by standard methods (Inoue, K. et al. *Plant Physiol.* 117, 761–770 (1998)). Protein concentrations were determined using the Bradford procedure (Bradford, M. M. *Anal Biochem.* 72, 248–254 (1976)).

Phenylpropanoid Analysis

Soluble and wall-bound phenolics in whole plant extracts as well as extracts of individual tissues were analyzed by HPLC (see Blount, et al. (2000)). The aqueous phase, which remained after ethyl acetate extraction of the wall-bound phenolics was lyophilized, and resuspended in 70% methanol for analysis. The HPLC eluates were monitored by absorbance at 270 nm, 310 nm and 550 nm and peaks were identified by comparison of retention times and uv spectra to those of known standards. Lignin was assayed by derivatization followed by reductive cleavage (Lu, F. C. and Ralph, J., *J. Ag. Food Chem.* 45, 2590–2592 (1997)).

Anthocyanin, Enzyme Activity, Phenylpropanoid, and Lignin Measurements

Figure 1:
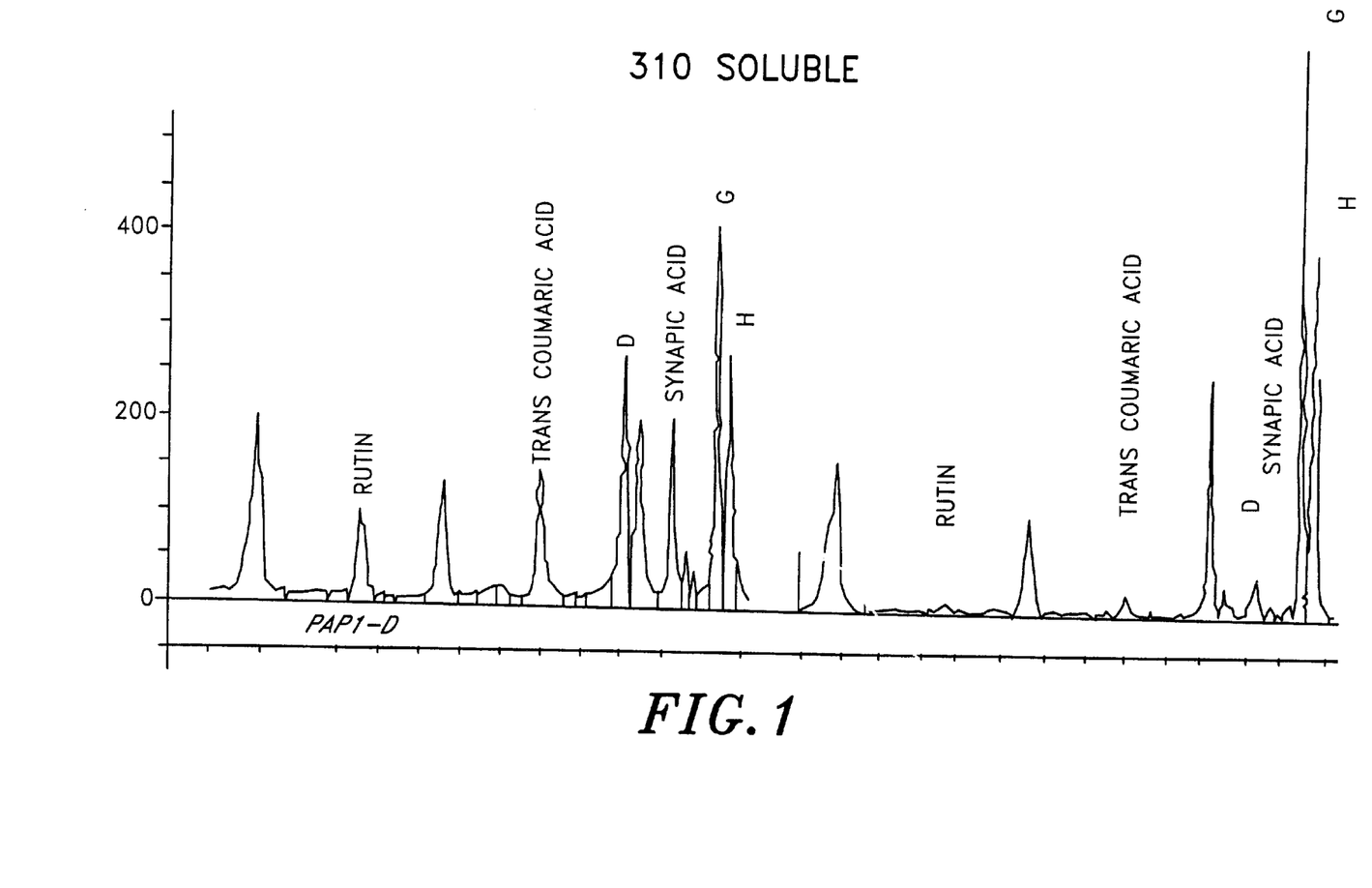
FIG. 1. Effect of the pap1-D mutation on the accumulation of phenylpropanoid products. HPLC profiles of phenylpropanoid metabolites in extracts from wild-type Col-0 (A, C, E) and pap1-D (B, D, F) plants. A, B, soluble phenolics; C, D, anthocyanidins, E, F, wall-bound phenolics.

To determine the extent of changes in anthocyanins and other phenylpropanoid-derived compounds in pap1-D, soluble and cell wall-bound phenolic compounds were extracted and analyzed by HPLC. Analysis of the soluble fraction, obtained by extraction in acetone, revealed several quantitative differences between pap1-D and wild-type Col-0 plants, in particular the increased levels of certain flavonol glycosides including Glc-Rha-quercetin, Glc-Rha-kaempferol and unidentified conjugates of kaempferol and quercitin (FIG. 1A,B). Following alkaline hydrolysis of the residue obtained after acetone extraction, one portion was freeze-dried for analysis of anthocyanidins (anthocyanin aglycones), and the remainder partitioned into ethyl acetate for determination of cell wall-bound hydroxycinnamic acids. There was a large increase in anthocyanidins in pap1-D compared to Col-0 (FIG. 1C,D). Striking increases were also seen in the levels of coumaric and sinapic acids in alkaline hydrolysates of the wall-bound phenolic fraction of pap1-D compared to Col-0 (FIG. 1E,F). Thus, pap1-D is characterized by strongly increased levels of glycosylated anthocyanins, flavonols and cell wall-esterified hydroxycinnamic acids, compared to wild-type Col-0.

The observation of increased wall-bound hydroxycinnamic acids in pap1-D prompted us to measure the content and composition of lignin, which is derived from hydroxycinnamic acid precursors. Lignin was analyzed by derivatization followed by reductive cleavage, which leads to information on the absolute levels of guaiacyl (G, monomethylated) and syringyl (S, di-methylated) lignin monomers. The results in Table 1 indicate that there was an increase in both total G and total S residues in the cell wall fraction of pap1-D compared to Col-0, but little difference in S/G ratio. The change in lignin monomers could reflect an increase in lignin content, or a change in composition leading to more efficient monomer extractability.

TABLE 1

Enhanced PAL activity and lignin levels in pap1-D plants

|  | Wild-type | pap1-D |
|---|---|---|
| PAL activity (mkrat/g FW) | 30.5 | 70.3 |
| COMT activity (μkat/g FW) | 44.2 | 44.4 |
| CCOMT activity (pkat/g FW) | 50.4 | 60.6 |

TABLE 1-continued

Enhanced PAL activity and lignin levels in pap1-D plants

|  | Wild-type | pap1-D |
|---|---|---|
| Lignin composition: |  |  |
| Total G ($\mu$mol/g) | 21.6 | 30.6 |
| Total S ($\mu$mol/g) | 2.5 | 5.0 |
| Total G & S ($\mu$mol/g) | 24.1 | 35.6 |
| S/G | 0.12 | 0.16 |

Changes in lignin content and composition have been engineered in transgenic plants by down-regulation of PAL, and of caffeic acid O-methyltransferase (COMT) and caffeoyl-CoA O-methyltransferase (CCOMT), enzymes of the lignin branch of phenylpropanoid biosynthesis PAL activity in stems of pap1-D plants was approximately twice that found in stems of wild-type plants, whereas there were little differences in the activities of the two O-methyltransferases (Table 1). Thus, the changes in lignin composition and increased levels of wall-bound sinapic acid in pap1-D reflect the change in PAL activity but do not appear to be associated with increases in lignin O-methyltransferase activities.

The Arabidopsis transparent testa glabarous1-1 (ttg1-1) mutation blocks anthocyanin accumulation and trichome formation. TTG1 encodes a WD40 repeat protein with homology to AN11 from petunia, which also controls anthocyanin production. To test the genetic relationship between TTG1 and PAP1, we crossed ttg1-1 with pap1-D. The pap1-D allele was tracked by Basta resistance and the ttg1-1 mutation was scored visibly. The double mutant F2 plants failed to accumulate anthocyanins indicating that TTG1 is required for the production of anthocyanins mediated by PAP1 overexpression, and acts either downstream of, or at the same step as, PAP1.

Anthocyanin content was higher in pap1-D plants over Col (Table 2). A 4-fold increase of anthocyanin was found under various light intensities. Enzyme activities of phenylpropanoid biosynthetic enzymes were compared between pap1-D and Col plants. The activity of phenylalanine ammonia lyase (PAL), the first committed step in the phenylpropanoid pathway, significantly increased in stem, cauline leaf, and root tissue (Table 2). HPLC analysis revealed an overall activation of phenylpropanoid biosynthesis in pap1-D plants with respect to both the complexity of the product array and the levels of the most abundant products (FIG. 1).

The levels of the flavonoid rutin and the simple phenolic acids, sinapic acid and trans coumaric acid were higher in pap1-D plants than Col (Table 2). The levels of the glucoside of p-coumaric acid were also substantially elevated. Moreover, the activation of phenylpropanoid biosynthesis extended to wall-bound as well as soluble products as judged by the levels of products released by base hydrolysis of the cell wall fraction. pap1-D plants also contained 2-fold more lignin of the t-S class than Col plants (Table 2). Taken together these results show that the pap1-D mutation causes a general upregulation of the phenylpropanoid pathway.

TABLE 2

Anthocyanins, Enzyme Activity, phenylpropanoid levels, and lignin content in various tissues shown as a ratio of pap1-D:Col.

|  | Stem | Rosette | Cauline | Root | Buds |
|---|---|---|---|---|---|
| Anthocyanins (A530/gFW) |  | 4.0 |  |  |  |
| PAL mkat/gFW | 2.3 | 0.8 | 2.1 | 2.9 | 1.3 |
| Coumaric Acid ug/gFW | 26.8 | 1.5 | 5.5 | 1.6 |  |
| Coumarate Conjugate ug/gFW | 5.6 | 2.3 | 3.8 | 1.1 |  |
| Synapic Acid ug/gFW | 5.2 | 2.1 | 2.5 | 0.4 |  |
| Ferulic Acid ug/gFW | 1.4 | 0.7 | 0.4 | 1.0 |  |
| Salicylic Acid (Free) |  | 0.25 |  |  |  |
| Salicylic Acid (Total) |  | 0.75 |  |  |  |
| c-G lignin | 1.0 |  |  |  |  |
| t-G lignin | 1.6 |  |  |  |  |
| c-S lignin | 1.8 |  |  |  |  |
| t-s lignin | 1.9 |  |  |  |  |

The ttg1 allele is a regulatory mutation that lacks pigmentation and does not express DFR. To test the genetic relationship between TTG1 and PAP1, the ttg1-1, pap1-D double mutant was made. In the F2 generation 1/4 of the Basta resistant plants had the ttg1-1 mutant phenotype, indicating that ttg1-1 is epistatic to pap1-D. TTG is thus required for the production of anthocyanins mediated by PAP1, and acts either downstream or in parallel to PAP1.

Example 4
Cloning of PAP1 (SEQ ID NO:1)

In a population of >100 segregating $T_2$ plants, each plant that had the pap1-D phenotype showed resistance to Basta, and all plants with a wild-type phenotype (i.e. lacking purple pigmentation) were sensitive to Basta, indicating that the mutation was tightly linked to the T-DNA insert. Moreover, hybridization of southern blots of pap1-D genomic DNA that had been digested with EcoRI or KpnI showed that the 35Se sequences were localized to single fragments of 10 and 12 kb respectively, indicating that the mutant contained a single, simple insertion. The 12 kb KpnI and 10 kb EcoR1 fragments were cloned by plasmid rescue as described below.

Figure 2A:
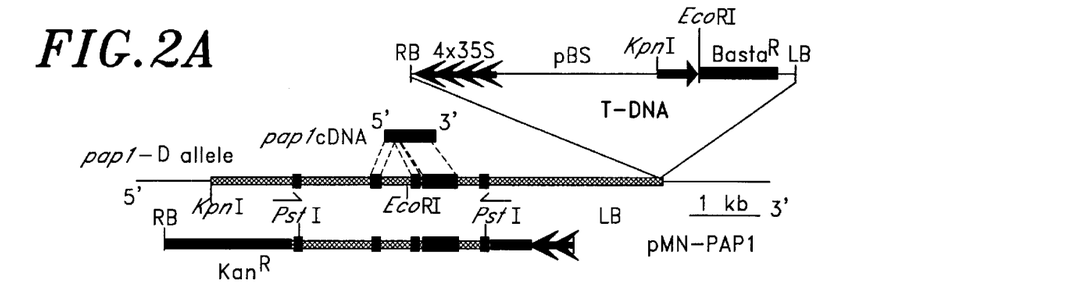
FIG. 2. Molecular characterization of PAP1. (A) Genomic context of T-DNA insertion in pap1-D and the pMN-PAP1 construct used for confirmation. (B) Sequence homology of R2R3 MYB domain proteins controlling anthocyanin production. Proteins were aligned using ClustalW. Dark shading is 100% conserved residues. Light shading matches PAP1. (C) phylogenetic tree showing Anthocyanin MYB family. The human gene c-myb is used as an outgroup.
Figure 2B:
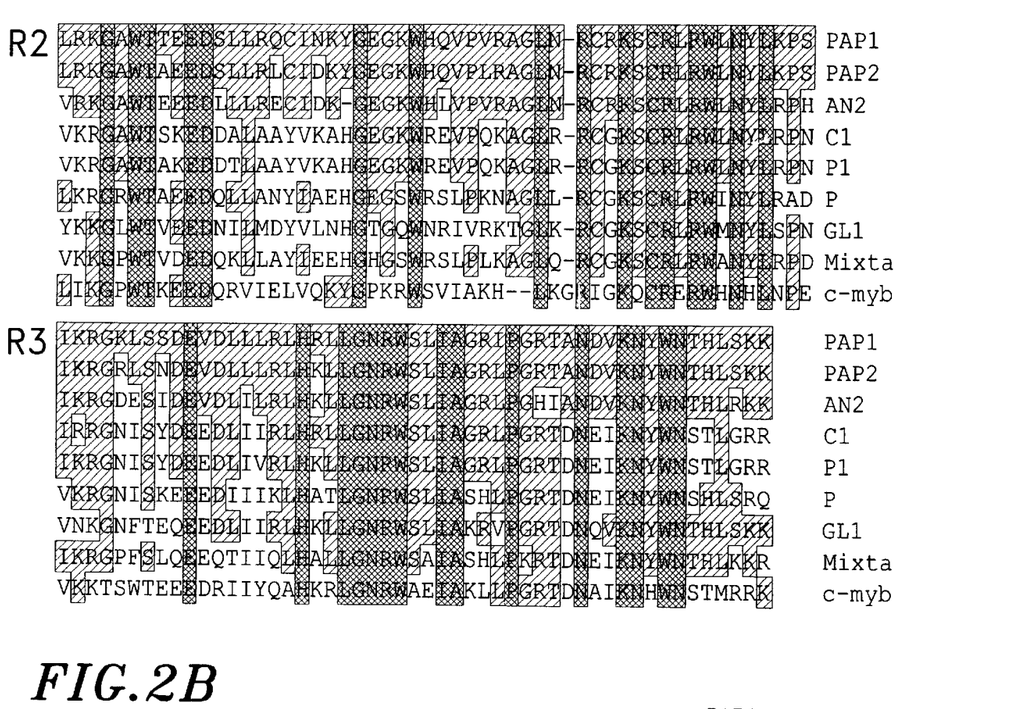

2 $\mu$g of pap1-D genomic DNA was digested with EcoRI or KpnI, purified, then ligated with T4 DNA ligase. Ligation reaction products were transformed into high competency SURE cells (Stratagene) by electroporation. Colonies from transformation of the KpnI and EcoRI ligation contained the 12 kb and 10 kb, pPAP1-K1 pPAP1-E1 plasmids. The location of the insertion is at 76646 bp of BAC F25P12. Plasmid rescue generated pPAP1-K1 and pPAP1-E1 respectively. Nucleotide sequencing and restriction analysis showed that the 12 kb KpnI fragment fully overlapped the smaller EcoR1 fragment. Probing the Arabidopsis CD4-7 cDNA library at high stringency with pPAP1-K1 resulted in the isolation of a single 956 bp cDNA which defined three exons in the genomic DNA of pPAP1-K1 encoding a MYB transcription factor (FIG. 2A,B). In the pap1-D line the 35Se sequences had inserted 5.1 kb 3' to the start of this gene, designated PAP1, and RNA blot hybridization with the PAP1 cDNA revealed a single 1 kb transcript which was massively overexpressed in the pap1-D mutant.

To confirm that overexpression of PAP1 caused the pap1-D phenotype a 3 kb genomic fragment spanning the three PAP1 exons and flanking sequences was cloned into pMN20-2, which contains two copies of the 35Se (ref. 5) creating pMN-PAP1. Transformation of wild type Col-0 with this construct, which mimics the genomic context of the pap1-D allele, generated multiple transgenic lines with the characteristic purple phenotype. As would be expected from position effects, these transgenic lines represented an allelic series ranging from wild-type to an even more intense phenotype than pap1-D, in some cases with strong purple pigmentation in the petals. In contrast, parallel transformation with pMN20-2 as an empty vector control gave no enhanced pigmentation phenotype.

Using the T-DNA as a probe in a Southern blot (see Example 3) a single band in pap1-D showed that the mutant contained a single, simple insertion. The 12 kb and 10 kb restriction fragments were cloned by plasmid rescue as follows:

Example 5
Sequence Homology Studies

Figure 2C:
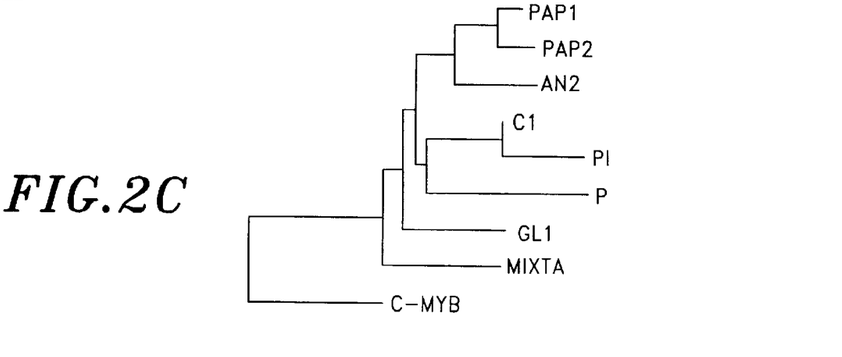

Sequence alignments with the Arabidopsis databases showed that PAP1 is a member of the R2, R3 MYB family, which is estimated to have >100 members in Arabidopsis and >80 in maize. PAP1 is identical to ATMYB75 except that ATMYB75 contains a sequencing error (1 bp deletion at 695) creating an early stop codon. The PAP1 proteins shares high homology with other MYB-like transcription factors that regulate anthocyanin production (FIG. 2B,C). The PAP1 is closely related to the product of the petunia AN2 gene, showing 82% identity through the MYB region and 50% identity overall. The products of the maize anthocyanin MYB genes C1 and p1 are 64% identical through the MYB region with 38% identity overall. The MYB transcription factor GLABAROUS1 from Arabidopsis and MIXTA from snapdragon control trichome development and are each 58% identical to PAP1 in the MYB domain and 33% identical overall. A phylogenetic tree constructed using these MYB protein shows that PAP1 belongs to a branch involved in anthocyanin biosynthesis (FIG. 2C).

Example 6
Identification of PAP2 (SEQ ID NO:3) by Database Searching

An EST, 193M15, with very high homology to PAP1 was also discovered in the Arabidopsis database. 193M15 encodes a protein with 93% identity to PAP1 in the MYB domain and 77% identity overall.

To determine if the protein encoded by 193M15 EST had a similar function to PAP1, a 35Spromoter:cDNA fusion construct, pCHF3:PAP2 was assembled as described in Example 7.

Example 7
Creation of pCHF3:PAP2, PMN-PAP1, 35S::PAP1. 35S::PAP2 Constructs

A PAP1 genomic fragment was amplified using

5'AACTACTGCAGCTAGAGCGTAGAGG (SEQ ID NO:9) and

5'TCAAACTGCAGAAACTAAGCCCA (SEQ ID NO:10)

to construct a 5' Pst and 3' Pst site. This fragment was cloned into a pMN20-2, which contains 2×35Se from the original Activation Tagging vector pSKI015. The PAP1 cDNA was amplified using 5' ACTGGTACCTTTTACAATTTGTTTA (SEQ ID NO:11) and

3' AAGGGATCCTATACACAAACGCA (SEQ ID NO:12)

cloned into the Kpn1 and BamH1 sites of pCHF3 ((pPZP211-based plant expression vector that carried the cauliflower mosaic virus 35S promoter and a pea ribulose 1,5-bisphosphate carboxylase/oxygenase terminator), creating pCHF3-PAP1. The PAP2 cDNA was produced by excising a DNA fragment from EST clone 193M15 using the KpnI and BamHI restriction enzymes. This DNA fragment was then cloned into the pCHF3 vector to create pCHF3-PAP2.

Transgenic plants overexpressing the PAP1 homologue were found to have purple leaves and stems although of a slightly weaker coloration than the pap1-D mutant or other pMN-PAP1 lines. The 193M15 gene was renamed PAP2 (SEQ ID NO:3).

Example 8
Chromosome Mapping

PAP1 and PAP2 mapped to 81 cM and 94 cM on chromosome 1, respectively. The PAP1 gene was mapped to 0.2 cM north of mi303 at 81.4 cM on Chromosome 1 using an Xba1 RFLP and the Col/Ler Recombinant Inbred Lines (Nottingham stock center). PAP1 is on BAC F25P12 just south of mi303. PAP2 is on BAC T24K10 near m315 on chromosome 1 about 13 cM below PAP1.

Example 9
Overexpression of PAP1 and PAP2 in Tobacco

To test whether expression of PAP1 or PAP2 can cause pigmentation in other plants, the PAP1 and PAP2 genes were overexpressed in the tobacco plant *Nicotiana tabacum xanthi*. Tobacco plants were generated that were transformed with the 35S:promoter:cDNA fusion constructs, pCHF3:PAP1 and pCHF3:PAP2, and pMN-PAP1 (see Example 7 for construction of these fusion constructs).

The pCHF3 control vector did not cause pigmentation in tobacco, whereas both pCHF3:PAP1 and pCHF3:PAP2 created purple tobacco plants. This indicated that the expression of the PAP1 or PAP2 genes activated production of anthocyanin pigments in a heterologous species. pMN-PAP1 transgenic tobacco also had increased pigmentation similar to pCHF3:PAP1 and pCHF3:PAP2. PAP1 and PAP2 overexpression caused a dramatic increase in tobacco floral pigmentation as well, compared to the control.

Example 10
Identification of Regulators of Secondary Metabolism

Plant produce natural products that have many pharmacological uses, such as chemotherapeutic agents like Taxol®, vinblastine and vincristine; antioxidants like sesamin and sesmolin; antifungals and antibacterials like hydoxycinnamaldehydes; pain killers such as morphine and other opiates; and the like. Further, certain flavonol glycosides and phenylpropanoid-substituted flavanols have hepatoprotective effects. Activation tagging in Arabidopsis represents a new approach to identifying regulators of secondary metabolism. PAP1 was found to control production of the visible anthocyanin pigments by regulating multiple biosynthetic enzymes. Regulators of branched pathways controlling production of other flavonoids can also be discovered to the extent that a means of observing their levels is available. The use of high-throughput HPLC to screen Activation Tagged Arabidopsis plants is a direct and efficient method for discovering other regulators. Thus, regulators identified in this way from Arabidopsis can be transferred into other crop plants where their function is conserved. As illustrated herein, the PAP1 and PAP2 genes function predictably in a heterologous species, such as tobacco plants.

Thus, when a key regulator of secondary metabolism is transferred into an appropriate medicinal plant, the production of bioactive natural products is enhanced. Tissue specific expression can also be used to increasing the production of plant-produced natural products, so that heterologous regulators can work with endogenous regulators to produce the desired compound at high levels. Some pMN-PAP1 transgenic lines did produce anthocyanin flavonoids in flower petals, a tissue that does not contain pigmentation in wild type Arabidopsis. This provides a natural and economical way to produce commercially significant quantities of important and normally nonabundant natural products in plants.

What is claimed is:

1. An isolated nucleic acid segment encoding the amino acid sequence of SEQ ID NO:2 operably linked to a heterologous promoter.

2. An isolated nucleic acid segment encoding the amino acid sequence of SEQ ID NO:4 operably linked to a heterologous promoter.

3. The isolated nucleic acid segment of claim 1, wherein the nucleic acid segment comprises the nucleotide sequence of SEQ ID NO:1.

4. The isolated nucleic acid segment of claim 2, wherein the nucleic acid segment comprises the nucleotide sequence of SEQ ID NO:3.

5. The isolated nucleic acid segment of claim 1 or 2, wherein the nucleic acid segment encodes a fusion protein.

6. A cell comprising the nucleic acid segment of claim 1 or claim 2.

7. A transgenic plant comprising a nucleic acid segment encoding the amino acid sequence of SEQ ID NO:2 or SEQ ID NO:4 under the control of a heterologous promoter.

8. The transgenic plant of claim 7, wherein the nucleic acid segment comprises the sequence of SEQ ID NO:1 or SEQ ID NO:3.

9. The transgenic plant of claim 7, wherein the plant is *Arabidopsis thaliana*.

10. The transgenic plant of claim 7, wherein the expression of the amino acid sequence of SEQ ID NO:2 or SEQ ID NO:4 is tissue specific.

11. The transgenic plant of claim 10, wherein the tissue is selected from the group consisting of, floral tissue, leaf, stem, root, cortex, meristem and cambium.

12. The transgenic plant of claim 7, wherein the amino acid sequence of SEQ ID NO:2 or SEQ ID NO:4 is expressed in floral organs.

13. The transgenic plant of claim 12, wherein the nucleic acid segment is located in a chromosomally-inserted transposon.

14. A system for expression of a gene of interest, the system comprising a nucleic acid segment encoding the amino acid sequence of SEQ ID NO:2 or SEQ ID NO:4 and a promoter comprising an anthocyanin myb binding site, wherein the promoter is operably linked to the gene of interest, wherein the product of the nucleic acid segment binds to the myb binding site and causes expression of the gene of interest.

\* \* \* \* \*

SEQUENCE LISTING

<160> NUMBER OF SEQ ID NOS: 11

<210> SEQ ID NO 1
<211> LENGTH: 956
<212> TYPE: DNA
<213> ORGANISM: Arabidopsis Thaliana

<400> SEQUENCE: 1

```
gtcgacccac gcgtccgttt acttatacct tttacaattt gtttatatat tttacgtatc      60
tatctttgtt ccatggaggg ttcgtccaaa gggctgcgaa aaggtgcttg gactactgaa     120
gaagatagtc tcttgagaca gtgcattaat aagtatggag aaggcaaatg gcaccaagtt     180
cctgtaagag ctgggctaaa ccggtgcagg aaaagttgta gattaagatg gttgaactat     240
ttgaagccaa gtatcaagag aggaaaactt agctctgatg aagtcgatct tcttcttcgc     300
cttcataggc ttctagggaa taggtggtct ttaattgctg gaagattacc tggtcggacc     360
gcaaatgacg tcaagaatta ctggaacact catctgagta agaaacatga accgtgttgt     420
aagataaaga tgaaaaagat agacattacg cccattccta caacaccggc actaaaaaac     480
aatgtttata agcctcgacc tcgatccttc acagttaaca acgactgcaa ccatctcaat     540
gccccaccaa aagttgacgt taatcctcca tgccttggac ttaacatcaa taatgtttgt     600
gacaatagta tcatatacaa caaagataag aagaaagacc aactagtgaa taatttgatt     660
gatggagata atatgtggtt agagaaattc ctagaggaaa gccaagaggt agatattttg     720
gttcctgaag cgacgacaac agaaaagggg gacaccttgg cttttgacgt tgatcaactt     780
tggagtcttt tcgatggaga gactgtgaaa tttgattagt gtttcgaaca tttgtttgcg     840
tttgtgtata ggtttgcttt cacctttaa tttgtgtgtt ttgataaata agctaatagt     900
ttttagcatt ttaatgaaat atttcaagtt tccgtgttaa aaaaaaaaaa aaaaaa       956
```

<210> SEQ ID NO 2
<211> LENGTH: 248
<212> TYPE: PRT
<213> ORGANISM: Arabidopsis Thaliana

<400> SEQUENCE: 2

```
Met Glu Gly Ser Ser Lys Gly Leu Arg Lys Gly Ala Trp Thr Thr Glu
 1               5                  10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110
```

```
Glu Pro Cys Cys Lys Ile Lys Met Lys Lys Ile Asp Ile Thr Pro Ile
        115                 120                 125

Pro Thr Thr Pro Ala Leu Lys Asn Asn Val Tyr Lys Pro Arg Pro Arg
130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245
```

```
<210> SEQ ID NO 3
<211> LENGTH: 1033
<212> TYPE: DNA
<213> ORGANISM: Arabidopsis thaliana

<400> SEQUENCE: 3
gtcgacccac gcgtccgtgg gaagccacaa taaccccta ttcctcggcc ttttttaaaa      60
aagttttaga ataatccgat aaaatacttt tatattaatt tttctttggt ccatggaggg     120
ttcgtccaaa gggttgagga aaggtgcatg gactgctgaa gaagatagtc tcttgaggct     180
atgtattgat aagtatggag aaggcaaatg gcatcaagtt cctttgagag ctgggctaaa     240
tcgatgcaga aagagttgta gactaagatg gttgaactat ttgaagccaa gtatcaagag     300
aggaagactt agcaatgatg aagttgatct tcttcttcgc cttcataagc ttctaggaaa     360
taggtggtcc ttgattgctg gtcgattgcc tggtcggacc gctaatgatg tcaaaaatta     420
ctggaacacc catctgagta aaaaacatga gtcttcgtgt tgtaagtcta aaatgaaaaa     480
gaaaaacatt atttcccctc ctacaacacc ggtccaaaaa atcggtgttt ttaagcctcg     540
acctcgatcc ttctctgtta acaatggttg cagccatctc aatggtctgc cagaagttga     600
tttaattcct tcatgccttg gactcaagaa aaataatgtt tgtgaaaata gtatcacatg     660
taacaaagat gatgagaaag atgattttgt gaataatcta atgaatggag ataatatgtg     720
gttggagaat ttactggggg aaaaccaaga agctgatgcg attgttcctg aagcgacgac     780
agctgaacat ggggccactt tggcgtttga cgttgagcaa ctttggagtc tgtttgatgg     840
agagactgtt gaacttgatt agtgtttctc accgtttgtt taagattgtg ggtggctttt     900
ctttcgtatt ttagtaatgt attttttctgt atgaagtaaa gaatttcagc attttaagaa     960
aaatggttat gtttctacgt aataaaaaaa aacgttattt ataaaaaaaa aaaaaaaaa     1020
aaaaaaaaaa aaa                                                      1033
```

```
<210> SEQ ID NO 4
<211> LENGTH: 249
<212> TYPE: PRT
<213> ORGANISM: Arabidopsis thaliana
<220> FEATURE:
<221> NAME/KEY: VARIANT
<222> LOCATION: (1)...(249)
```

-continued

<223> OTHER INFORMATION: Xaa = Any Amino Acid

<400> SEQUENCE: 4

Met Glu Gly Ser Ser Lys Gly Leu Arg Lys Gly Ala Trp Thr Ala Glu
1               5                   10                  15

Glu Asp Ser Leu Leu Arg Leu Cys Ile Asp Lys Tyr Gly Glu Gly Lys
            20                  25                  30

Trp His Gln Val Pro Leu Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
50                  55                  60

Arg Leu Ser Asn Asp Glu Val Asp Leu Leu Arg Leu His Lys Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Ser Ser Cys Cys Lys Ser Lys Met Lys Lys Asn Ile Ile Ser
        115                 120                 125

Pro Ser Thr Thr Pro Val Gln Lys Ile Gly Val Phe Lys Pro Arg Pro
130                 135                 140

Arg Ser Phe Ser Val Asn Asn Gly Cys Ser His Leu Asn Gly Leu Pro
145                 150                 155                 160

Xaa Val Asp Leu Ile Pro Ser Cys Leu Gly Leu Lys Lys Asn Asn Val
                165                 170                 175

Cys Glu Asn Ser Ile Thr Cys Asn Lys Asp Asp Glu Lys Xaa Asp Phe
            180                 185                 190

Val Asn Asn Leu Met Asn Gly Asp Asn Met Trp Leu Glu Asn Leu Leu
        195                 200                 205

Gly Glu Asn Gln Glu Ala Xaa Ala Ile Val Pro Glu Ala Thr Thr Ala
    210                 215                 220

Glu His Gly Ala Thr Leu Ala Phe Asp Val Glu Gln Leu Trp Ser Leu
225                 230                 235                 240

Phe Asp Gly Lys Thr Val Glu Leu Asp
                245

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide to Arabidopsis thaliana
      sequence

<400> SEQUENCE: 5
tggtctccgt ccttccgtca a                                              21

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide to Arabidopsis thaliana
      sequence

<400> SEQUENCE: 6
ccctcaaatg tccgtctatg gaa                                            23

-continued

```
<210> SEQ ID NO 7
<211> LENGTH: 24
<212> TYPE: DNA
<213> ORGANISM: Artificial Sequence
<220> FEATURE:
<223> OTHER INFORMATION: Oligonucleotide to Arabidopsis thaliana
      sequence

<400> SEQUENCE: 7
ctatacgctt acctaccaac aaac                                             24

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide to Arabidopsis thaliana
      sequence

<400> SEQUENCE: 8
tctccgatga gaagtagcac caa                                              23

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide to Arabidopsis thaliana
      sequence

<400> SEQUENCE: 9
aactactgca gctagagcgt agagg                                            25

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide to Arabidopsis thaliana
      sequence

<400> SEQUENCE: 10
tcaaactgca gaaactaagc cca                                              23

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide to Arabidopsis thaliana
      sequence

<400> SEQUENCE: 11
actggtacct tttacaattt gttta                                            25
```